US 6,699,263 B2

(12) United States Patent
Cope

(10) Patent No.: US 6,699,263 B2
(45) Date of Patent: Mar. 2, 2004

(54) SLIDING SUTURE ANCHOR

(75) Inventor: Constantin Cope, Elkins Park, PA (US)

(73) Assignee: Cook Incorporated, Bloomington, IN (US)

( * ) Notice: Subject to any disclaimer, the term of this patent is extended or adjusted under 35 U.S.C. 154(b) by 33 days.

(21) Appl. No.: 10/116,991

(22) Filed: Apr. 5, 2002

(65) Prior Publication Data

US 2003/0191497 A1 Oct. 9, 2003

(51) Int. Cl.[7] ............................................. A61B 17/04
(52) U.S. Cl. ....................................... 606/232; 606/153
(58) Field of Search .................................. 606/232, 153

(56) References Cited

U.S. PATENT DOCUMENTS

| 3,521,640 A | 7/1970 | Carey et al. |
| 3,938,501 A | 2/1976 | Erikson |
| 4,006,747 A | 2/1977 | Kronenthal et al. |
| 4,077,412 A | 3/1978 | Moossun |
| 4,235,238 A | 11/1980 | Ogiu et al. |
| 4,580,568 A | 4/1986 | Gianturco |
| 4,669,473 A | 6/1987 | Richards et al. ............ 606/232 |
| 4,674,506 A | 6/1987 | Alcond |
| 4,960,424 A | 10/1990 | Grooters |
| 5,035,706 A | 7/1991 | Giantureo et al. |
| 5,071,405 A | 12/1991 | Piontek et al. |
| 5,123,914 A | 6/1992 | Cope ............................ 606/232 |
| RE34,021 E | 8/1992 | Mueller et al. |
| 5,141,516 A | 8/1992 | Detweiler |
| 5,507,767 A | 4/1996 | Maeda et al. |
| 5,690,656 A | 11/1997 | Cope et al. |
| 5,741,685 A | 4/1998 | Vacanti |
| 5,800,456 A | 9/1998 | Maeda et al. |
| 6,004,348 A | 12/1999 | Banas et al. |
| 6,110,183 A | 8/2000 | Cope ............................ 606/232 |
| 6,200,336 B1 | 3/2001 | Pavcnik et al. |
| 6,309,413 B1 | 10/2001 | Dereume et al. |
| 6,313,372 B1 | 11/2001 | Suzuki |
| 6,322,494 B1 | 11/2001 | Bullivant et al. |
| 6,332,879 B1 | 12/2001 | Nielsen et al. |
| 6,626,919 B1 * | 9/2003 | Swanstrom ................. 606/153 |

* cited by examiner

Primary Examiner—Gary Jackson
(74) Attorney, Agent, or Firm—Brinks Hofer Gilson & Lione

(57) ABSTRACT

A method and the apparatus for anastomosing two hollow viscera that can be performed percutaneously or through the patients mouth. The apparatus includes an anchor assembly including a stationary T-bar anchor secured to the distal end of a suture and a sliding anchor that is attached to the suture proximal to the stationary T-bar anchor. The sliding anchor is held in place on the suture but can be slid along the suture when pressure is applied to it. The anchor assembly is inserted through the abdominal wall, into the stomach, and then through the stomach into the jejunum. The stationary anchor is then released into the jejunum and the sliding anchor is released in the stomach. A pusher is then used to push or slide the sliding anchor distally until the tissue between the stationary and sliding anchors are in close contact. After the anchor has been placed, the suture can be severed at the sliding anchor.

20 Claims, 5 Drawing Sheets

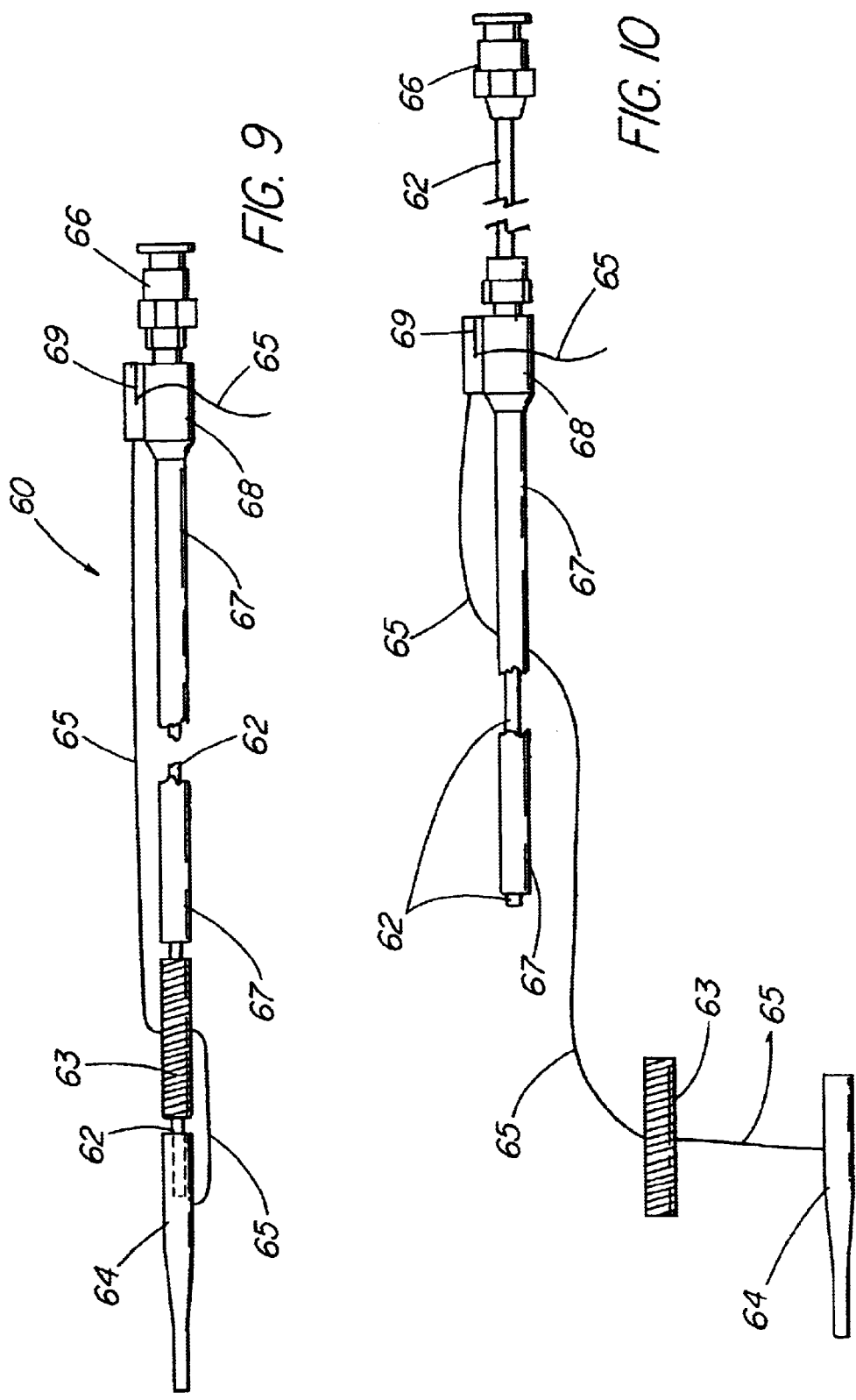

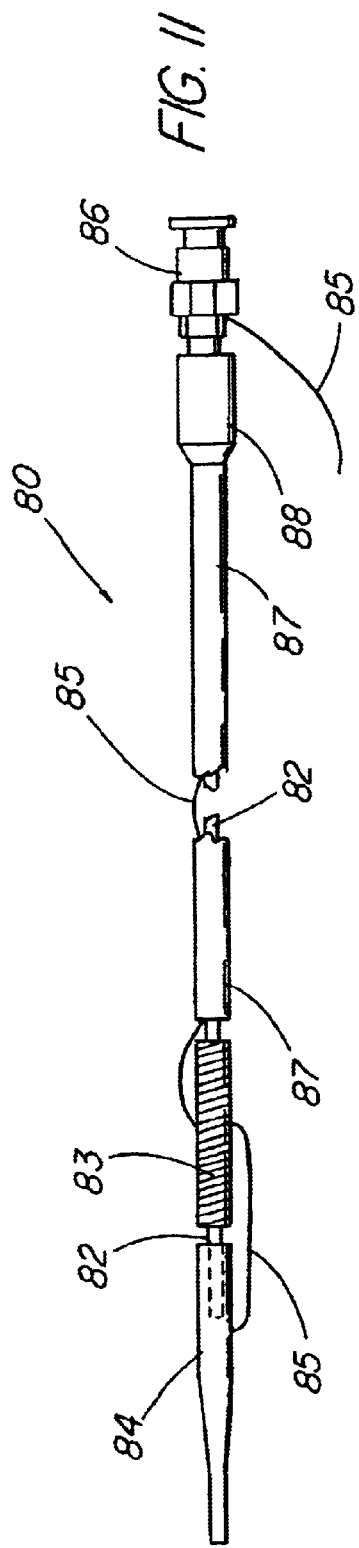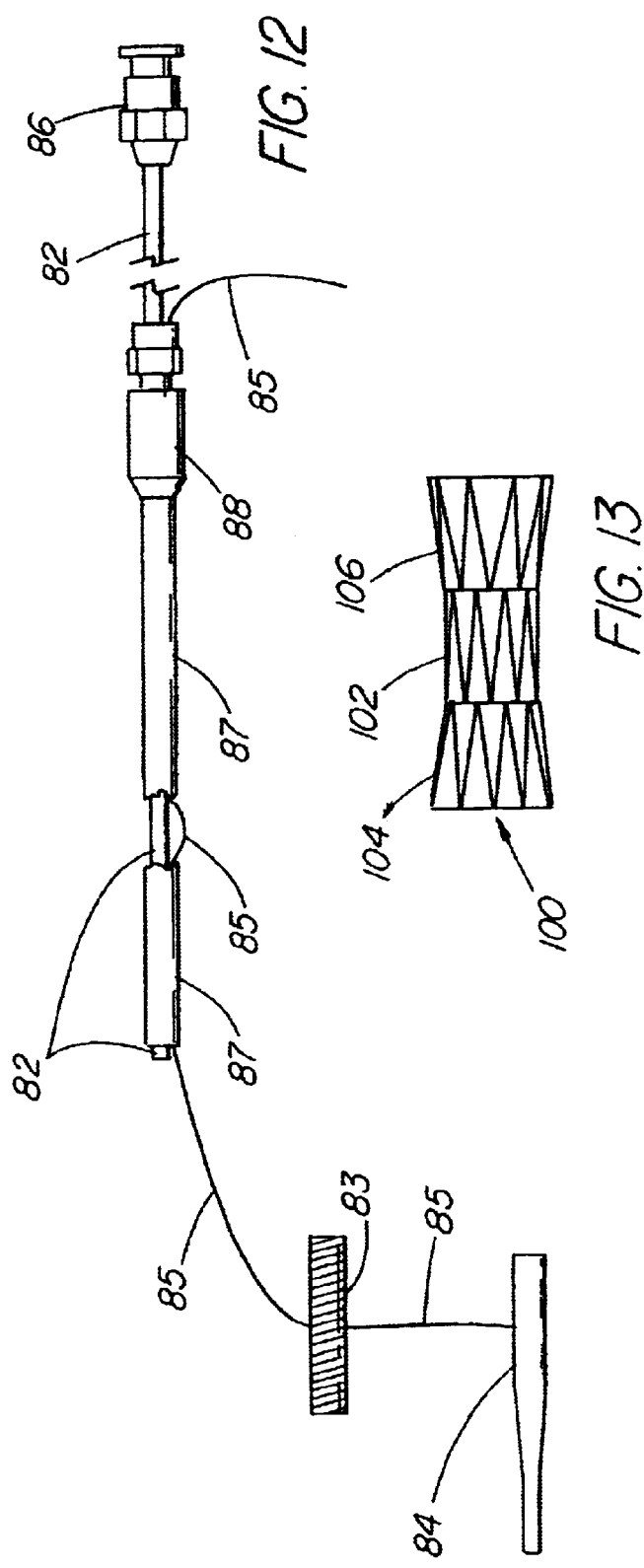

SLIDING SUTURE ANCHOR

BACKGROUND OF THE INVENTION

Because of the invasive nature of traditional surgery there are inherent risk and objectionable side effects associated therewith. For example if a patient is found to have an inflammatory stricture in the small intestine and it is decided to surgically remove the section of the intestine containing the stricture and reconnect the severed ends of the intestine by sutures. Such invasive surgery requires a general anesthesia, is time consuming, expensive and is painful and requires a long healing process. As a result less invasive procedures are being developed as alternatives to traditional surgical procedures.

Draining viscera, such as the stomach or gall bladder, can be performed through a track inserted percutaneous into the viscera, however, there is the danger that gastric juices, bile or infected fluids could spill into the peritoneal cavity. To prevent this, procedures and devices have been developed to pull and anchor the wall of the viscera into contact with the abdominal wall using sutures anchor devices that are inserted into the cavity of the viscera through thin hollow needles. With the viscera thus stabilized with its wall held flush against the abdominal wall, drain tubes can be inserted into the viscera without the danger of spillage into the peritoneal cavity. Examples of viscera anchor of this type are shown in U.S. Pat. Nos. 5,123,914 and 6,110,183. The anchors disclosed in U.S. Pat. Nos. 5,123,914 and 6,110,183 are constructed to prevent damage to the interior of the viscus and can be inserted and removed through small diameter needles.

Another method and device, now in use, that avoid the trauma of traditional surgery, is a method and apparatus for creating abdominal visceral anastomoses. This method and device, is disclosed in U.S. Pat. No. 5,690,656, uses a pair of powerful magnets, each having a raised rim around their perimeter. The patient swallows one magnet, then waits until it has worked its way into the jejunum, then the patient swallows the second magnet which works its way into the stomach. The location of the magnets can be monitored and manipulated such that they become attracted to each through the walls of the stomach and the jejunum. The magnets apply pressure to the tissue that is held between the raised rims. After a few days, the tissue between the magnets becomes necrotic and the two magnets together pass into the jejunum and eventually pass through the bowel. A stent can then be endoscopically placed in the resulting opening, to prevent the opening from closing. The procedure disclosed in U.S. Pat. No. 5,690,656, although less invasive than traditional surgery, extends over a several day period and the precise placement of the magnets is problematic. Thus, a one-step procedure and apparatus for anastomosing two hollow viscera by a percutaneous technique in which the surgeon has greater control over the location of the anastomosis is needed.

SUMMARY OF THE INVENTION

The present invention relates to a method and the apparatus for anastomosing two hollow viscera using a technique that is an improvement over the method and apparatus discussed above. This technique can be performed percutaneously but could also be performed through the patients mouth. The suture anchor is modified by adding a T-bar to the suture that can be caused to slide along the suture to a position proximal to the stationary suture anchor that is located at the distal end of the suture. A hollow needle containing this improved anchor assembly devise pierces the patient's abdominal wall, extends into the stomach and then through the stomach into the jejunum. The stationary anchor, carried at the distal end of the suture, is then released into the jejunum and the needle is withdrawn back into the stomach where the sliding anchor is released from the needle. The needle is then withdrawn leaving the suture extending from the anchors out through the needle hole in the abdominal wall. The needle is then replaced, over the suture, by a small dilator/pusher. The pusher is then used to push or slide the sliding anchor distally until the tissue between the stationary and sliding anchors are in close contact. After the anchor has been placed, the suture can be severed at the sliding anchor. Depending upon the size and location of the viscera between which the anastomosis is to be formed, the number of anchors that will be placed may be one or multiple. In the example disclosed herein, several anchors were placed to create an area of tissue contact between the outer surfaces of the viscera. This area of tissue contact is then penetrated by another needle and a wire guide is placed through this newly created aperture, over which a sheath dilator combination is placed. The size of the puncture formed in the area of tissue contact is enlarged and a stent is placed through the puncture. The stent can be a Z-type stent which is a self-expanding stent formed of stainless steel wire that is arranged in a closed zigzag pattern. The Z-stent is compressed into a reduced size shape so that it can be placed in passageway in a patient by means of a sheath. Reference may be made to U.S. Pat. No. 4,580,568 for a completed disclosure of a Z-stent.

This technique for anastomosing two hollow viscera has advantages over the method disclosed in U.S. Pat. No. 5,690,656 since it is much faster, it being completed in one visit as opposed to at least two visits that are days apart. Also, this method allows the surgeon more control over the exact location of the anastomosis.

BRIEF DESCRIPTION OF THE DRAWINGS

FIG. 9 is an illustration of another embodiment of the invention showing the anchor assembly carried by a cannula that extends through a pusher and the suture is external of the pusher.

FIG. 10 is an illustration of the embodiment shown in FIG. 9 after the anchor assembly has been released from the cannula.

FIG. 11 is an illustration of another embodiment of the invention showing the anchor assembly carried by a cannula that extends through a pusher and the suture is internal of the pusher.

FIG. 12 is an illustration of the embodiment shown in FIG. 11 after the anchor assembly has been released from the cannula.

FIG. 13 is an illustration of the type of stent that is placed in the anastomosis.

DETAILED DESCRIPTION OF THE INVENTION

Hereinafter, embodiments of the present invention will be described with reference to the accompanying drawings; however, the present invention is not limited to the embodiments described below.

This invention concerns a technique, using a sliding anchor 30, for anastomosing two hollow viscera. The invention will be illustrated and will be described, with reference to a percutaneous technique for anastomosing the stomach 10 and the jejunum 12 through the body wall. However, the same technique could be performed through the patients mouth by using a gastroscope with appropriately sized equipment. Other applications for this technique are for example cholecystoduodenostomy, cholecystodochotom, choledochogastrostomy, ileocolostomy, portocaval shunt, and percutaneous colostomy.

Figure 1:
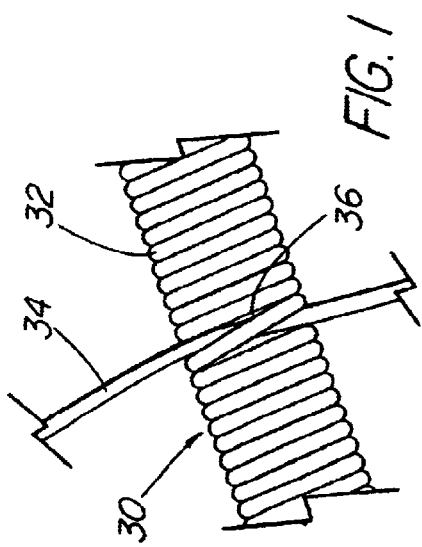
FIG. 1 is a perspective view of the sliding anchor with the coils of the spring closed around the suture.
Figure 2:
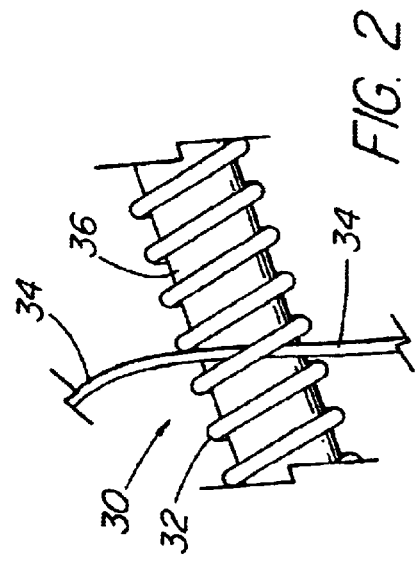
FIG. 2 is a perspective view of the sliding anchor with the coils of the spring opened to better show the suture that is held between the spring and the mandrel.

An embodiment of the sliding anchor 30 will be described with reference to FIGS. 1 and 2. The sliding anchor as seen in FIG. 1 comprises a segment of a hollow helical spring 32 that is about ¾ to 1¼ inches long and a mandrel 36. The helical spring 32 has an outer diameter of about 0.038 inches in diameter which is the type of springs used in some conventional guide wires. A suture 34 is pushed between two coils near the center of the spring 32 such that the suture extends through the coil spring between two adjacent coils, wraps around one of these coils and extends out of the coil spring on opposite sides of the coil that it has wrapped around. After the suture has been wrapped around the coil the cylindrical-shaped mandrel 36, having a diameter of about 0.018 inches is inserted within the hollow helical spring 32. In FIG. 2, the spring 32 has been expanded to better show the relationship between the spring 32, suture 34 and mandrel 36. As can be best seen in FIG. 2, the spring 32 exerts pressure on the suture 34 against the mandrel 36. This pressure results in friction that resists relative movement of the suture 34 relative to the spring 32. It should be noted that when the spring is in its normal unexpanded state, as seen in FIG. 1, the suture is also pinched between adjacent coils of the spring 32 which results in additional friction and further resists relative movement of the suture 34 relative to the spring 32. However, when a sufficient force is applied, the anchor 30 can be slid along the suture 34. The mandrel also functions to provide rigidity to the central portion of the anchor 30, and by utilizing a mandrel that is shorter than the spring 32, it allows the anchor 30 to have floppy tips. As best seen in FIG. 1, this attachment of the sliding anchor to the suture 34 allows the suture 34 to extend perpendicular to the axial extent of the spring 32.

The force required to start the anchor 30 sliding on the suture 34 should be about 250–300 grams but in some situations should be as high as 500 grams. The desired force can be changed by increasing the diameter of the mandrel 36, for example to 0.022 inches, by using a tighter coil spring 32, a larger gauge suture, or a more tacky suture.

Figure 3:
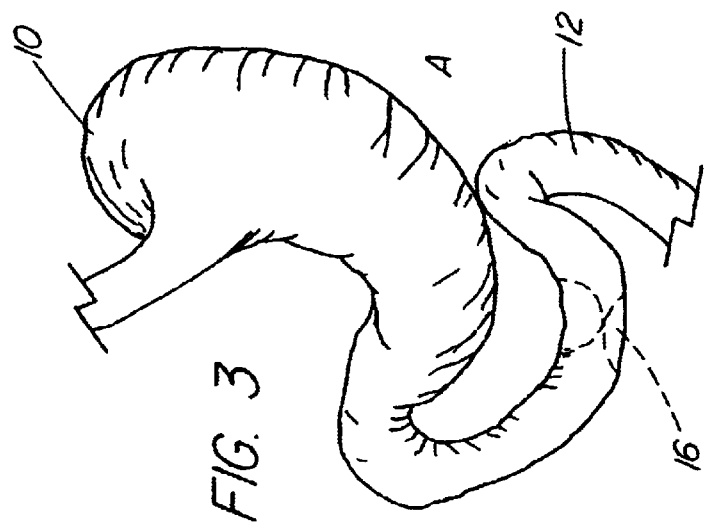
FIG. 3 is a perspective illustration of the stomach and the jejunum.

Refer now to FIG. 3, where the relative positions of several organs of the abdominal cavity are shown including the stomach 10 and the jejunum 12. In FIG. 3, the jejunum is shown as having an inflammatory stricture 16 formed therein which obstructs passage through the jejunum 12. This obstruction will be bypassed by anastomosing the wall of the stomach 10 and the jejunum 12 at a point in the jejunum beyond the inflammatory stricture 16. In FIG. 3, the area where the anastomosis will be formed is indicated by the letter A.

Preliminary to performing the anastomosing technique, a sheath 50 could be inserted percutaneously into the stomach 10 to opacify the proximal jejunum with air and a contrast medium.

Figure 4:
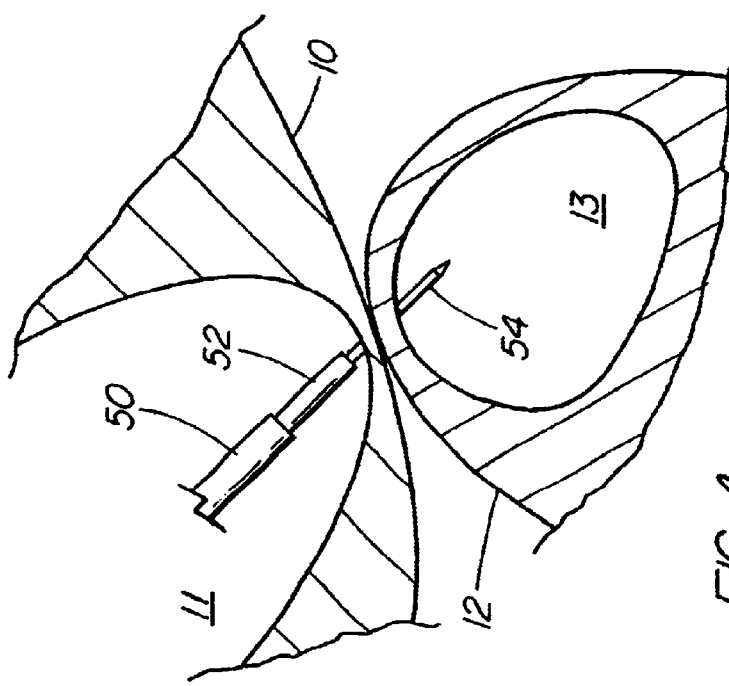
FIG. 4 is an enlarged view of the anastomosis area.

FIG. 4 is an enlargement of the area A where the anastomosis will be formed with portions of the stomach 10 and jejunum 12 walls broken away so that the interior of these viscera can be viewed.

Figure 5:
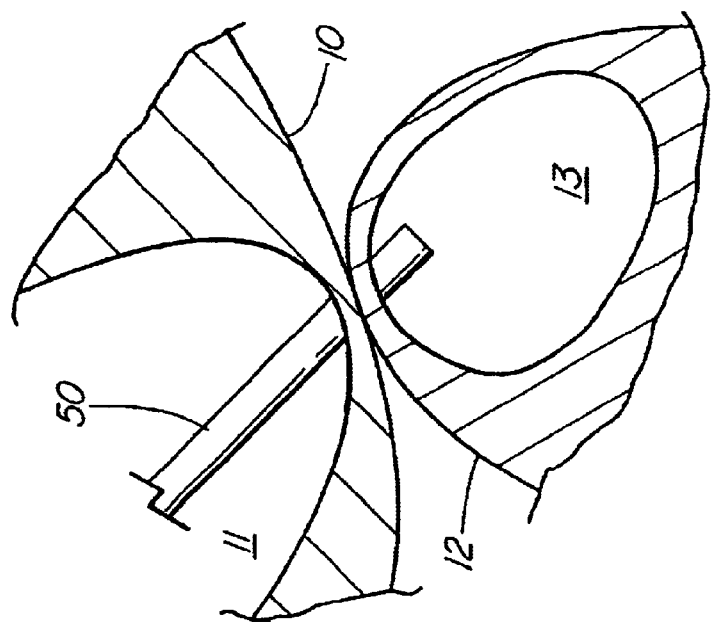
FIG. 5 is similar to FIG. 4 with the cannula and stylet withdrawn.

Refer now to FIG. 4, which is an enlarged view of the area A where the anastomosis is to be formed. Portions of the proximal walls of the stomach and jejunum have been broken away so that the interior of these viscera are visable. A 5.5 Teflon catheter 50 has been prepared with a telescoping 19 ga cannula 52 that carries a pointed stylet 54. The body wall (not shown) is penetrated with this instrument as well as the wall of the stomach 10. As seen in FIG. 4, the catheter 50 and the cannula 52 have penetrated one wall of the stomach 10 and are in the stomach cavity 11. In this view, the stylet 54 has penetrated the opposite stomach wall and also the wall of the jejunum 12 such that the distal end of the stylet 54 is in the interior of the jejunum 12. In the next step, the catheter 50 and the cannula 52 follow the stylet 54 and penetrates into the cavity 13 of the jejunum 12. In FIG. 5, the cannula 52 and stylet 54 have been withdrawn and the distal end of the catheter 50 is in the cavity 13 of the jejunum 12.

Figure 6:
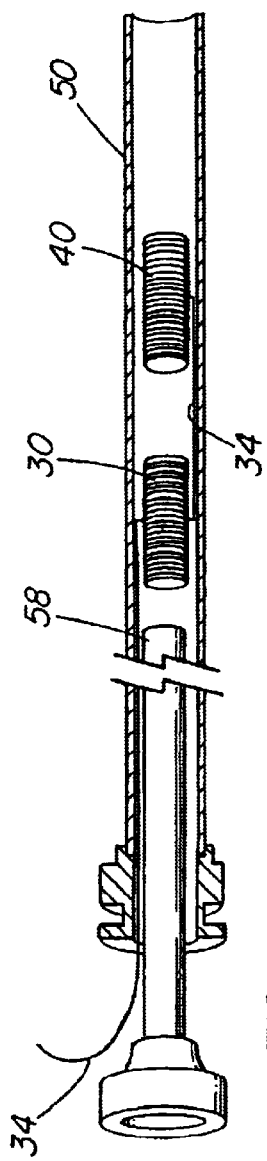
FIG. 6 is a cross-section view of the catheter with the anchor assembly.
Figure 7A:
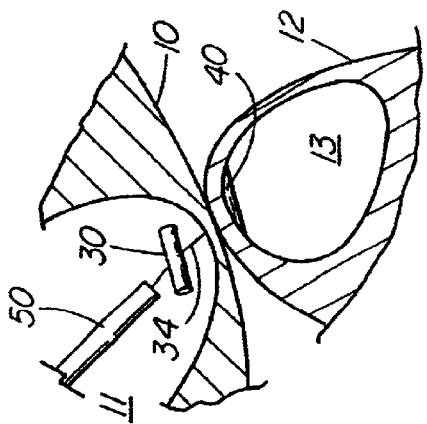
FIG. 7A is a view similar to FIGS. 4, 5 and 7 showing how the sliding anchor is pushed along the suture to secure it to the stomach lining.
Figure 7:
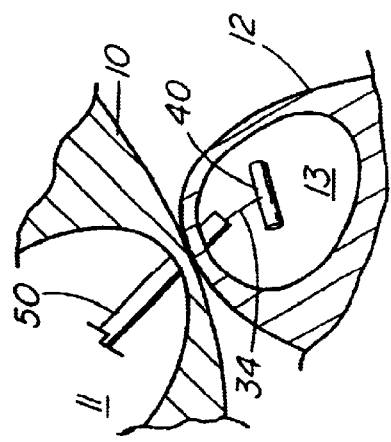
FIG. 7 is a view similar to FIGS. 4 and 5 with a stationary anchor in the jejunum.

Shown in FIG. 6 is a cross-section view of the catheter 50 into which the anchor assembly has been loaded. The assembly is loaded in series with the stationary anchor 40 having the distal end of a suture 34 secured to its midportion followed by the sliding anchor 30 of the type shown in FIGS. 1 and 2. The stationary anchor 40 is loaded first into the catheter 50 and, thus, will exit first from the distal end of the catheter 50. The other end of the suture 34 extends out through the proximal end of the catheter 50. A pusher rod 58 is used to push the anchors 40 and 30 through the catheter 50. FIG. 7, which is similar to FIGS. 4 and 5 shows the stationary anchor 40 after it has been pushed out the distal end of catheter 50 by the pusher rod 58. Suture 34 which is secured to stationary anchor 40 extends into the lumen of catheter 50. The catheter 50 is then pulled back such that its distal end is in the stomach cavity 11 from which location the sliding anchor 30 is pushed out with the pusher rod 58. The catheter 50 is then used to push the sliding anchor 30 toward the stationary anchor 40 while the suture that extends out the proximal end of the catheter 50 is held taut. FIG. 7A is a view similar to FIGS. 4, 5 and 7 showing how the sliding anchor 30 is pushed by the catheter 50 causing it to slide along the suture 34 until it is flush against the stomach lining. When the anchors 40 and 30 have been brought together, the stomach and jejunum walls are held flush together between the anchors.

Figure 8:
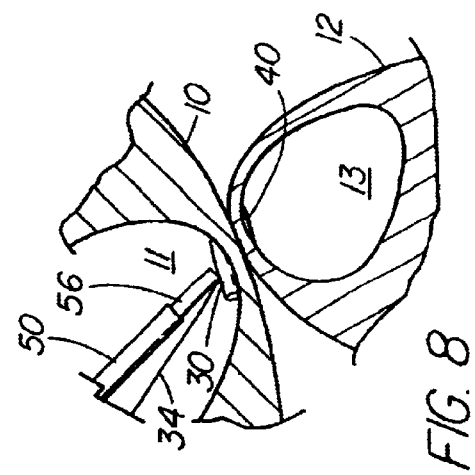
FIG. 8 is a view similar to FIGS. 4, 5, 7 and 7A in which the suture is being cut by a cannula with a sharp edge after the sliding anchor has been pushed into place against the stomach lining.

Once the anchors are locked together, the pusher rod 58 can be removed from the catheter 50 and, as illustrated in FIG. 8, a cannula 56 with a sharp distal edge can be threaded over the suture 34 to cut the suture 34 adjacent the sliding anchor 30. The process of sliding the sliding anchor 30 toward the stationary anchor and then cutting the suture 34 is referred to as placing the anchor. In time, the suture 34 holding the anchors together will deteriorate and the anchors 30 and 40 will be released from each other. The anchors 30 and 40 will then be free to be passed through the bowel.

It is also contemplated to construct the anchors from a plastic which will dissolve after several weeks when visceral adhesion has been well established.

The above procedure is repeated one or more times to install additional pairs of anchors around the anastomosis area A. When the visceral walls are securely held together by multiple pair of anchors the area between the multiple anchors can be needled, a guide wire inserted and the tract can be safely dilated and a large stent inserted.

An example of the type of stent that could be used in this situation is illustrated in FIG. 13. A three-section stent 100 of the type disclosed in the above-identified U.S. Pat. No. 5,282,824 is shown in FIG. 13. The central section 102 of the stent actually stents or crosses the anastomosis and is designed to expand to the desired diameter of the anastomosis. The outer sections 104 and 106 of the stent extend one on each side, are connected to the central section, and extend beyond the anastomosis. The outer sections 104 and 106 are designed to expand to a diameter greater than the desired diameter of the anastomosis. However, their connections to the central section restrict their expansion at this connection. The outer ends of sections 104 and 106 are free to expand to their full extent and, thus, function to secure the central section 102 of the stent in place. After the stent 100 has been placed in the anastomosis and permitted to expand, it forms a "grommet"-shaped stent that will resist being expelled from the anastomosis. Each section of the stent comprises a sleeve and a plurality of struts that are connected to one another at joints and are also attached to the sleeve. The sleeve can be formed of nylon or other plastic material, but a preferred material is a synthetic rubber film such as a styrene-type elastomer film, e.g., stylene isoprene stylene (SIS). In this three-section stent 100, the end sections 104 and 106 can function with or without sleeves.

Another embodiment of applicant's invention is shown in FIGS. 9 and 10. The assembly 60 of this embodiment shown in FIG. 9 is inserted through a catheter (not shown) to the area where the anastomosis will be formed. Assembly 60 includes a cannula 62, connected at its proximal end to a fitting 66, that extends through lumens formed in the sliding anchor 63 and the stationary anchor 64. In the previous embodiment, the mandrel 36 is disclosed as a solid rod. In this embodiment, the mandrel for the sliding anchor 63 is formed of a tube to provide a lumen through which the cannula 62 can pass. The cannula 62 also functions as a central stiffening member for the assembly 60. A hollow pusher rod 67 telescopes over the cannula 62. The pusher rod 67 is secured to a fitting 68 at its proximal end. In this embodiment, the suture 65 is external of the assembly 60. The suture 65 is secured at its distal end to the stationary anchor 64 and is attached to the sliding anchor 63 such that the sliding anchor can be slid along the suture 65 in response to a force applied to the sliding anchor 63. A V-slot or notch 69 is formed in the pusher rod fitting 68 into which the suture 65 can be placed to releasably secure suture 65 to the fitting 68.

The assembly 60 is guided through a catheter (not shown), similar to catheter 50 of the embodiment shown in FIGS. 1–8, to the area where the anastomosis is to be formed. The assembly 60 is advanced through the catheter such that the stationary anchor 64 is located in the distal viscera. The cannula 62 is then withdrawn from within the stationary anchor 64, which releases the stationary anchor 64 into the distal viscera thus separating it from the remainder of the assembly 60. The suture 65 is released from the notch 69 and pulled taut which pulls the stationary anchor 64 into a position where it is flush against the wall of the distal viscera. The suture 65 is secured in the notch 69 to maintain the suture 65 taut. The cannula 62 is withdrawn further, releasing the sliding anchor 63 into the proximal viscera and thus releasing the sliding anchor from the remainder of the assembly 60. At this stage of the procedure, as illustrated in FIG. 10, the anchors 63 and 64 have been released from assembly 60 and are carried by the suture 65. The suture 65 is maintained taut which causes the sliding anchor 63 to assume an attitude parallel to the stationary anchor 64 which is held flat against the wall of the distal viscera. It should be noted that the suture 65, although exterior of the pusher rod 67, is interior of the catheter which is not shown in FIGS. 9 and 10. The pusher rod 67 is advanced while maintaining the suture 65 taut. When the pusher rod 67 is advanced, its distal end engages the sliding anchor 63 causing it to slide along suture 65 until it is flush against the wall of the proximal viscera. When the sliding anchor 63 has been advanced toward the stationary anchor 64 such that the walls of the distal and proximal viscera are held snugly between the anchors, tension on the suture 65 can be released and the sliding anchor will retain its position on the suture 65. Both the cannula 62 and the pusher rod 67 can now be removed from the catheter. A cannula with a sharp distal edge can then be advanced through the catheter to sever the suture 65 at the sliding anchor 63, as illustrated in FIG. 8 for the embodiment illustrated in FIGS. 1–8.

Another embodiment of applicant's invention is shown in FIGS. 11 and 12. The assembly 80 of this embodiment, shown in FIG. 11, is inserted through a catheter (not shown) to the area where the anastomosis will be formed. Assembly 80 includes a cannula 82 connected at its proximal end to fitting 86 which extends through lumens formed in the sliding anchor 83 and the stationary anchor 84. As in the embodiment illustrated in FIGS. 9 and 10, the mandrel for the sliding anchor 83 is formed of a tube to provide a lumen through which the cannula 82 can pass. The cannula 82 also functions as a central stiffening member for the assembly 80. A hollow pusher rod 87 telescopes over the cannula 82. The pusher rod 87 is secured at its proximal end to a fitting 88. In this embodiment, the suture 85 is internal of the pusher rod 87. The distal end of suture 85 is secured to the stationary anchor 84 near its mid-portion and is connected to the sliding anchor 83, such that the sliding anchor 83 can be slid along the suture 85 in response to a force applied to the sliding anchor 83. The proximal end of suture 85 is held between the fittings 86 of the cannula 82 and 88 of the pusher rod 87.

The assembly 80 is guided through a catheter (not shown), similar to the catheter of the embodiment disclosed in FIGS. 1–8, to the area where the anastomosis is to be formed. The assembly 80 is advanced to the anastomosis area such that the stationary anchor 84 is located in the distal viscera. The cannula 82 is then withdrawn from the stationary anchor 84 which releases the stationary anchor 84 into the distal viscera and from the remainder of the assembly 80. Withdrawing the cannula 82, relative to the pusher rod 87, releases the suture 85 from between the fittings 86 and 88 which permits suture 85 to be pulled taut and to move the stationary anchor flush against the wall of the distal viscera. The cannula 82 is withdrawn further, releasing the sliding anchor 83 into the proximal viscera and thus releasing the sliding anchor from the remainder of the assembly 80. At this stage of the procedure, as illustrated in FIG. 12, the anchors 83 and 84 have been released from assembly 80 and are carried by the suture 85. The suture 85 is maintained taut which causes the sliding anchor 83 to assume an attitude parallel to the stationary anchor 84 which is being held flat against the wall of the distal viscera. The pusher rod 87 is then advanced through the catheter while maintaining the suture 85 taut. When the pusher rod 87 is advanced, its distal end engages the sliding anchor 83 causing it to slide along suture 85 until it is flush against the wall of the proximal viscera. When the sliding anchor 83 has been advanced toward the stationary anchor 84 such that the walls of the distal and proximal viscera are held snugly between the anchors, the tension on the suture 85 can be released and the sliding anchor will retain its position on the suture 85. The cannula 82 and pusher rod 87 can be withdrawn over the suture 85 from within the catheter. A cannula with a sharp distal edge 56 can then be advanced through the catheter to sever the suture 85 at the sliding anchor 83, as illustrated in FIG. 8 for the embodiment illustrated in FIGS. 1–8.

EXAMPLE

Method Used for Experimental Gastroenterostomy in Swine

The following procedure was performed and results were obtained on three swine.

A 10F sheath was inserted percutaneously in the inflated stomach of the swine to opacify the proximal jejunum with air and to provide a contrast medium.

A second 10F gastrostomy sheath was inserted percutaneously in the stomachs of the swine through which a 5.5F Teflon catheter was inserted which punctured the back wall of the stomach and extended into the jejunum. A single gastric anchor was inserted in the jejunum and a guide wire was advanced into the small bowel.

An anchor assembly, consisting of a stationary anchor secured to the distal end of a suture and a sliding anchor attached to the suture proximal to the stationary anchor, was advanced through the 5.5F Teflon catheter which extended through the back wall of the stomach and into the jejunum at a location to one side of the guide wire. The stationary anchor was pushed out of the catheter with a catheter pusher and deposited into the jejunum. The catheter was then pulled back into the stomach where the sliding anchor was pushed out into the stomach and pushed along the suture to a position snug against the gastric wall. The suture was cut proximally of the sliding anchor. The above procedure was repeated several times to place multiple anchors between the stomach and jejunum walls at locations surrounding the area where the anastomosis was to be formed. These anchors maintained the apposition of the gastric and jejunal walls while the aperture in these walls through which the guide wire extended was dilated and a stent was inserted without intraperitoneal leakage.

At postmortem examination, 6–12 days later, there was excellent visceral adhesion at the anastomosis around the stent.

While the invention has heretofore been described in detail with particular reference to illustrated apparatus, it is to be understood that variations, modifications, and the use of equivalent mechanisms can be effected without departing from the scope of this invention. It is, therefore, intended that such changes and modifications be covered by the following claims.

It is intended that the accompanying drawings and foregoing detailed description is to be considered in all respects as illustrative and not restrictive. The scope of the invention is intended to embrace any equivalents, alternatives, and/or modifications of elements that fall within the spirit and scope of the invention, and all changes which come within the meaning and range of equivalency of the claims are therefore intended to be embraced therein.

What is claimed is:

1. A method for forming an anastomosis between first and second adjacent hollow viscera, comprising the steps of:
    (a) selecting the area where the anastomosis is to be formed;
    (b) providing a tract from outside of the body, to the interior of the first hollow viscus and through the adjacent walls of the first and second hollow viscera in the area where the anastomosis is to be formed;
    (c) providing an anchor assembly comprising a suture having a stationary anchor secured to its distal end and a sliding anchor slidably attached to the suture proximal to the stationary anchor;
    (d) attaching said sliding anchor to said suture such that it does not move relative to the suture unless a force is applied to the sliding anchor in a direction longitudinally along the suture;
    (e) positioning the anchor assembly, through said tract, in the area where the anastomosis is to be formed;
    (f) depositing said stationary anchor in said second hollow viscus;
    (g) depositing said sliding anchor in said first hollow viscus;
    (h) placing the anchor by applying a force to said sliding anchor through said track to position said sliding anchor against the wall of said first hollow viscus with the adjacent walls of the viscera held flush together between the stationary and sliding anchors;
    (i) providing a tract from outside of the body, through which the anastomosis is to be formed, to the area where the anastomosis is to be formed and adjacent to where the walls of the viscera have been anchored together;
    (j) piercing the adjacent walls of the hollow viscera in the area where the anastomosis is to be formed and adjacent to where the anchor was placed;
    (k) dilating the aperture formed by piercing the adjacent walls of the hollow viscera to form the anastomosis of the size desired.

2. The method for forming an anastomosis as set forth in claim 1 wherein:
    (l) repeating steps (a) through (h) to place multiple anchors in the area where the anastomosis is to be formed.

3. The method for forming an anastomosis as set forth in claim 1 wherein said sliding anchor is created by:
    providing a length of coil spring and a cylindrical-shaped mandrel that can be received within the coil spring; and
    passing the suture through adjacent coils of the coil spring such that the suture wraps around a coil and is engaged between the coil that it wraps around and the coils on opposite sides of the coil that it wraps around;
    providing a mandrel of a size that can be inserted in the length of coil spring;
    inserting the mandrel in the coil spring such that the mandrel is in engagement with the portion of the suture that is wrapped around the coil spring.

4. The method for forming an anastomosis as set forth in claims 1 or 2 or 3 wherein the method further includes the step of:

(m) severing the portion of the suture that is distal of the placed anchor.

5. The method for forming an anastomosis as set forth in claims 1 or 2 or 3 wherein the method further includes the step of:
   (n) placing a stent in the dilated aperture formed in the adjacent walls of the hollow viscera.

6. The method for forming an anastomosis as set forth in claims 1 or 2 or 3 wherein the force applied to said sliding anchor to position said sliding anchor against the wall of said first hollow viscus is in the range of 250–500 grams.

7. The method for forming an anastomosis as set forth in claims 1 or 2 or 3 wherein the following additional steps are performed:
   (o) providing stationary and sliding anchors that have elongated shapes;
   (p) securing said sutures to the elongated stationary anchor at a mid-portion of the elongated stationary anchor; and
   (q) attaching said suture to the elongated sliding anchor at a mid-portion of the elongated sliding anchor.

8. The method for forming an anchor between first and second adjacent hollow viscera, comprising the steps of:
   (a) selecting the area where the anchor is to be formed;
   (b) providing a tract from outside of the body, to the interior of the first hollow viscus and through the adjacent walls of the first and second hollow viscera in the area where the anchor is to formed;
   (c) providing an anchor assembly comprising a suture having a stationary anchor secured to its distal end and a sliding anchor slidably attached to the suture proximal to the stationary anchor;
   (d) attaching said sliding anchor to said suture such that it does not move relative to the suture unless a force is applied to the sliding anchor in a direction longitudinally along the suture
   (e) positioning the anchor assemble, through said tract, to the area where the anchor is to be formed;
   (f) depositing said stationary anchor in said second hollow viscus;
   (g) depositing said sliding anchor is said first hollow viscus;
   (h) placing the anchor by applying a force to said sliding anchor, through said track, to position said sliding anchor against the wall of said first hollow viscus with the adjacent walls of the viscera held flush together between the stationary and sliding anchors.

9. The method for forming an anchor between first and second adjacent hollow viscera, comprising the steps of as set forth in claim 8 wherein said sliding anchor is created by:
   providing a length of coil spring and a cylindrical-shaped mandrel that can be received within the coil spring; and
   passing the suture through adjacent coils of the coil spring such that the suture wraps around a coil and is engaged between the coil that it wraps around and the coils on opposite sides of the coil that it wraps around;
   providing a mandrel of a size that can be inserted in the length of coil spring;
   inserting the mandrel in the coil spring such that the mandrel is in engagement with the portion of the suture that is wrapped around the coil spring.

10. The method for forming an anchor as set forth in claims 8 or 9 wherein the method further includes the step of:
    (n) severing the portion of the suture that is distal of the placed anchor.

11. The method for forming an anchor as set forth in claims 8 or 9 wherein the force applied to said sliding anchor to position said sliding anchor against the wall of said first hollow viscus is in the range of 250–500 grams.

12. The method for forming an anchor as set forth in claims 8 or 9 wherein the following additional steps are performed:
    (o) providing stationary and sliding anchors that have elongated shapes;
    (p) securing said sutures to the elongated stationary anchor at a mid-portion of the elongated stationary anchor; and
    (q) attaching said suture to the elongated sliding anchor at a mid-portion of the elongated sliding anchor.

13. A device for percutaneously placing an anchor between the walls of a first and second adjacent hollow viscera, comprising:
    a tract that extends percutaneously from outside of the body, to the interior of the first hollow viscus and through the adjacent walls of the first and second hollow viscera in the area where the anchor is to be placed;
    an anchor assembly, comprising a suture having a stationary anchor secured to its distal end and a sliding anchor slidably attached to the suture proximal to the stationary anchor;
    the attachment of said sliding anchor to said suture being such that the sliding anchor will not move relative to the suture unless a force is applied to the sliding anchor in a direction longitudinally along the suture;
    said stationary and sliding anchors being dimensioned to be received sequentially in said tract such that they can be slid through the tract to the area where the anchor is to be placed with the stationary anchor leading and the sliding anchor following;
    a force applying mechanism that can extend through said track to the area where the anchor is to be placed at which it can engage the sliding anchor and apply a force thereto to slide the sliding anchor longitudinally along the suture;
    said sliding anchor being attached to said suture such that it does not move relative to the suture unless a force is applied to the sliding anchor in a direction longitudinally along the suture.

14. A device for percutaneously placing an anchor between the walls of a first and second adjacent hollow viscera, as set forth in claim 13 further comprising:
    the attachment of said sliding anchor to said suture being such that the sliding anchor will not move relative to the suture unless a force in the range of 250–500 grams applied to the sliding anchor in a direction longitudinally along the suture.

15. A device for percutaneously placing an anchor between the walls of a first and second adjacent hollow viscera, as set forth in claims 13 or 14 further comprising:
    said sliding anchor comprising a length of coil spring and a cylindrical-shaped mandrel that can be received within the coil spring; and
    the attachment of the coil spring to the suture is accomplished by passing the suture through adjacent coils of the coil spring such that the suture wraps around a coil and is engaged between the coil that it wraps around and the coils on opposite sides of the coil that it wraps around, and the mandrel is within the coil spring in engagement with the portion of the suture that is wrapped around the coil spring.

16. A device for percutaneously placing an anchor between the walls of a first and second adjacent hollow viscera, as set forth in claims 13 or 14 and further comprising:

a suture severing mechanism having a sharp distal edge that can be advanced through the catheter to the area where the anchor is to be placed to sever the suture at the sliding anchor after the anchor has been placed.

17. A device for percutaneously placing an anchor between the walls of a first and second adjacent hollow viscera, as set forth in claims 13 or 14 and further comprising:

said stationary and sliding anchors that have elongated shapes;

said suture secured to the elongated stationary anchor at a mid-portion of the elongated stationary anchor; and said suture secured to the elongated sliding anchor at a mid-portion of the elongated sliding anchor.

18. A device for percutaneously placing an anchor between the walls of a first and second adjacent hollow viscera, as set forth in claim 15 and further comprising:

said length of coil spring having an outside diameter of about 0.038 inch and said cylindrical-shaped mandrel having a diameter of about 0.018 inches.

19. A device for percutaneously placing an anchor between the walls of a first and second adjacent hollow viscera, as set forth in claim 16 and further comprising:

said length of coil spring having an outside diameter of about 0.038 inch and said cylindrical-shaped mandrel having a diameter of about 0.018 inches.

20. A device for percutaneously placing an anchor between the walls of a first and second adjacent hollow viscera, as set forth in claim 17 and further comprising:

said length of coil spring having an outside diameter of about 0.038 inch and said cylindrical-shaped mandrel having a diameter of about 0.018 inches.

* * * * *